United States Patent [19]

DeLuca et al.

[11] 4,226,787

[45] Oct. 7, 1980

[54] FLUOROVITAMIN D COMPOUNDS AND PROCESSES FOR THEIR PREPARATION

[75] Inventors: Hector F. DeLuca; Heinrich K. Schnoes; Joseph L. Napoli, Jr.; Bruce L. Onisko, all of Madison, Wis.

[73] Assignee: Wisconsin Alumni Research Foundation, Madison, Wis.

[21] Appl. No.: 64,212

[22] Filed: Aug. 6, 1979

Related U.S. Application Data

[62] Division of Ser. No. 928,279, Jul. 26, 1978, abandoned.

[51] Int. Cl.$^2$ .......................... C07J 9/00; C07J 21/00
[52] U.S. Cl. .................................................. 260/397.2
[58] Field of Search ..................................... 260/397.2

[56] References Cited

U.S. PATENT DOCUMENTS

| | | | |
|---|---|---|---|
| 3,959,320 | 5/1976 | Salmond | 260/397.2 |
| 4,098,801 | 7/1978 | Micheli | 260/397.2 |

*Primary Examiner*—Elbert L. Roberts
*Attorney, Agent, or Firm*—Howard W. Bremer

[57] ABSTRACT

Fluorine-substituted vitamin D compounds, methods for preparation of such compounds and fluorinated intermediate compounds used in such methods are disclosed. The fluorine-substituted vitamin D compounds are characterized by vitamin D-like activity in stimulating intestinal calcium transport and bone mobilization and in promoting the calcification of rachitic bone.

4 Claims, No Drawings

FLUOROVITAMIN D COMPOUNDS AND PROCESSES FOR THEIR PREPARATION

The invention described herein was made in the course of work under a grant or award from the Department of Health, Education and Welfare.

This application is a division of 928,279, July 26, 1978, abandoned.

This invention relates to compounds having vitamin D-like activity. More specifically, this invention relates to fluoro-derivatives of vitamin D.

Vitamins $D_3$ and $D_2$ are well-known agents for the control of calcium and phosphorus homeostasis. These compounds, in the normal animal or human, stimulate intestinal-calcium transport and bone-calcium mobilization and are effective in preventing rickets. Research during the past decade has shown, however, that vitamins $D_2$ and $D_3$ must be metabolized to their hydroxylated forms before biological activity is expressed. Current evidence indicates, for example, that 1,25-dihydroxyvitamin $D_3$, the dihydroxylated metabolite of vitamin $D_3$ is the compound responsible for the biological effects mentioned earlier. Similarly, 1,25-dihydroxyvitamin $D_2$ is the active form of vitamin $D_2$.

We have now found that fluorinated vitamin D compounds also possess vitamin D-like activity. These fluoro-analogs, therefore, represent useful compounds for the treatment of various diseases such as osteomalacia, osteodystrophy, and hyperparathyroidism.

This invention relates to fluorovitamin D compounds and to fluoro-5,6-trans-vitamin D compounds possessing vitamin D-like activity, and to fluorinated intermediates used for their preparation.

Specifically this invention relates to fluorovitamin D compounds of general structure I below, and 5,6-trans-fluorovitamin D compounds of general structure II below,

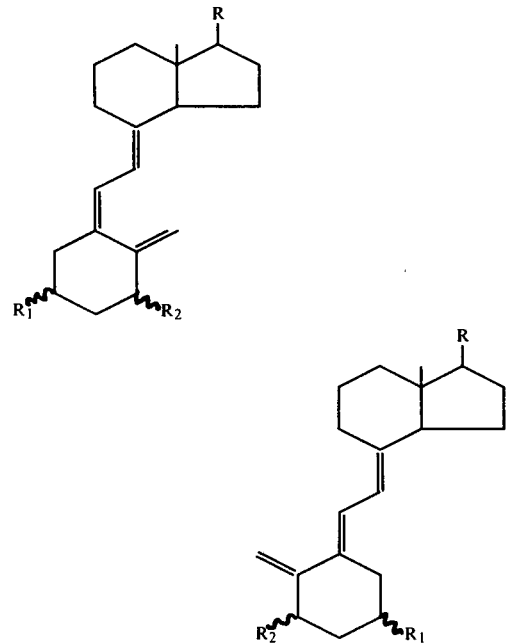

where R represents a steroid side chain of the configuration

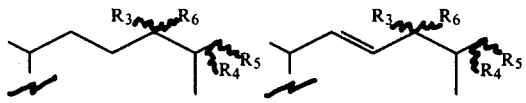

and where $R_1$ is selected from the group consisting of hydrogen, hydroxyl, O-lower alkyl or O-acyl, and where $R_2$, $R_3$, $R_4$ and $R_5$ are selected from the group consisting of hydrogen, hydroxyl, O-lower alkyl, O-acyl, or fluoro except that at least one of $R_2$, $R_3$, $R_4$, or $R_5$ must be fluoro, and where $R_6$ represents hydrogen or lower alkyl.

These fluoro compounds are prepared by a process which involves the treatment of a hydroxyvitamin D compound or hydroxyvitamin D analog with a fluorinating agent and obtaining directly the corresponding fluorovitamin D compound or fluorovitamin D analog in which fluorine is located at the carbon originally occupied by the hydroxy function(s) of the starting material.

Suitable starting materials for this fluorination process include hydroxyvitamin D compounds of general structure III below, or hydroxy-5,6-trans-vitamin D compounds of general structure IV, below, or hydroxy-3,5-cyclo-vitamin D compounds of general structure V below,

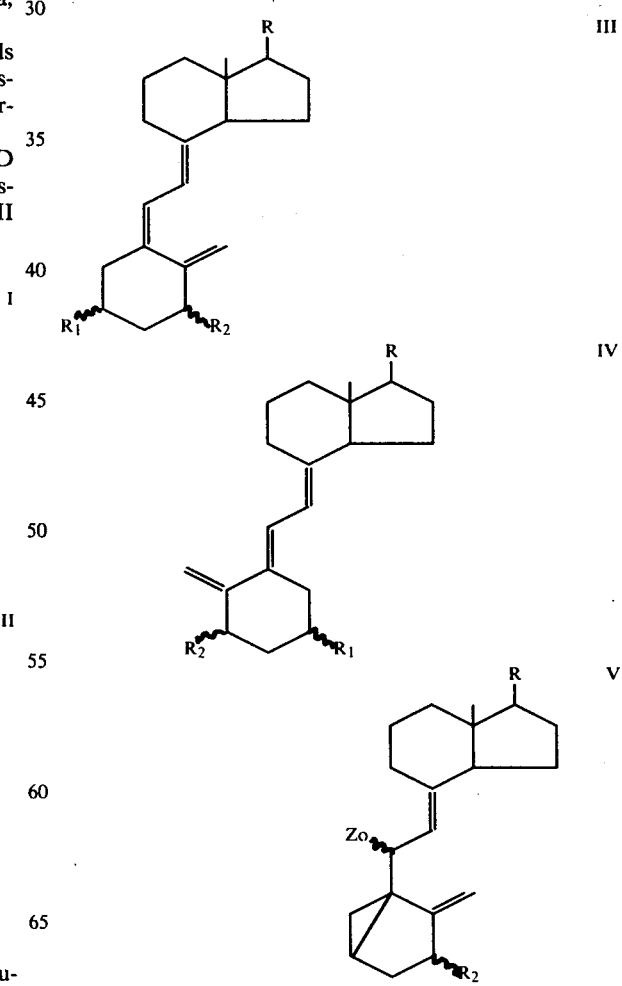

where R represents a steroid side chain of the configuration

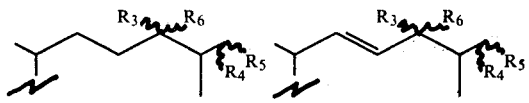

and where $R_1$ is selected from the group consisting of hydrogen, hydroxy, O-lower alkyl, and O-acyl, and where $R_2$, $R_3$, $R_4$ and $R_5$ are selected from hydrogen, hydroxyl, O-lower alkyl, and O-acyl, except that at least one of $R_2$, $R_3$, $R_4$ or $R_5$ must be hydroxy, and where $R_6$ represents hydrogen or lower alkyl, and where Z represents lower alkyl.

In this specification and in the claims the words "lower alkyl" denotes a hydrocarbon radical containing from 1 to about 5 carbon atoms which may be of normal or branched chain configuration (e.g. methyl, ethyl, isopropyl) and the word "acyl" denotes an aliphatic acyl group containing 1 to about 5 carbon atoms (e.g. acetyl, propionyl) or an aromatic or substituted aromatic acyl group (e.g. benzoyl or nitro-benzoyl).

Fluorovitamin D compounds of general structure I are prepared from starting materials of general structure III, whereas fluoro-5,6-transvitamin D compounds of structure II are prepared from compounds of general structure IV, and fluorination of cyclovitamin D starting materials of general structure V, followed by subsequent conversions as described hereinafter leads to both fluorinated products I and II.

The starting materials for fluorination, e.g. compounds of general structures III-V can be prepared by known methods. Hydroxyvitamin D compounds of general structure III are available by synthesis or as isolated natural products (see for example, Schnoes and DeLuca, in *Bioorganic Chemistry*, E. E. Van Tamelen, ed., Vol. 2., Chap. 12, pp. 299–335, Academic Press, N.Y., 1978). The 5,6-trans-vitamin D compounds of general structure IV can be prepared from the corresponding 5,6-cis compounds (general structure III) by the well-known isomerization reaction using iodine catalyst [Verloop et al., *Rec. Trav. Chim. Pays-Bas.* 78, 1004 (1969)].

3,5-Cyclovitamin D compounds of general structure V can be prepared by the procedures of Sheves and Mazur, J. Am. Chem. Soc. 97, 6249 (1975), and Paaren et al., Proc. Nat. Acad. Sci. USA 75, 2080 (1978).

Jones et al (U.S. Pat. No. 4,069,321) have claimed the preparation of various side chain fluorinated vitamin $D_3$ derivatives and side chain fluorinated dihydrotachysterol$_3$ analogs. The method of preparation suggested by these investigators involves fluorination of a precursor steroid and subsequent conversion of the fluorosteroid to the desired fluorovitamin D compound.

It has now been found, however, that side chain and-/or ring A-fluorinated vitamin D compounds or analogs of general structures I and II above can be much more conveniently prepared by direct introduction of fluorine into intact hydroxyvitamin D compounds and analogs of general structures III-V above, by means of fluorinating reagents such as a dialkylaminosulfur trifluoride, e.g. diethylaminosulfur trifluoride. With such reagents, one or more fluorine substituents can be introduced into a vitamin D molecule, by direct replacement of hydroxy function(s) in the starting material.

Middleton [J. Org. Chem. 40, 574 (1975)] has described the use of diethylaminosulfur trifluoride for the displacement of hydroxy functions by fluorine in organic compounds, but his applications are limited to simple and stable molecules, which provide no basis for judging the efficacy of the reagent for direct introduction of fluorine into vitamin D compounds without alteration of the sensitive triene chromophore. There is indeed only one previous application of diethylaminosulfur trifluoride for the direct synthesis of 25-fluorovitamin $D_3$ from 25-hydroxyvitamin $D_3$ [see Onisko, Schnoes, and DeLuca, *Tetrahedron Letters* (no. 13) 1107 (1977)]. It is this chemical reactivity of the vitamin D chromophore that has led other investigators skilled in the art to adopt indirect and laborious routes when attempting the synthesis of fluorovitamin D compounds. For example, Jones et al. (U.S. Pat. No. 4,069,321) in suggesting methods for the preparation of several fluorovitamin D analogs, use diethylaminosulfur trifluoride only for the introduction of fluorine into precursor steroids which are subsequently converted to the fluorovitamin D analogs.

It has now been found that the aforesaid diethylaminosulfur trifluoride reagent can be used for the introduction of fluorine at various positions (e.g. carbon-24, 25, 26) of the side chain of a vitamin D molecule, as well as for the introduction of fluorine at carbon 1, and readily permits the preparation of all the fluorovitamin D compounds of the Jones et al. patent (referenced above) more efficiently and directly.

Direct successful fluorination at carbon 1 of the vitamin D molecule is particularly noteworthy and surprising because available information suggested that the vitamin triene chromophore, which is highly prone to rearrangement, would undergo undesirable and irreversible alteration attendant upon fluorine introduction at carbon 1. Indeed the seemingly analagous reaction, namely, introduction of fluorine at carbon 3 by treating a C-3-hydroxyvitamin $D_3$ compound or analog with diethylaminosulfur trifluoride is not successful precisely because of chromophore rearrangment. Displacement of the hydroxy function at that position with diethyaminosulfur trifluoride leads to an undesired product in which the chromophore is altered. The facile preparation of 1-fluorovitamin D compounds and vitamin D analogs is, therefore, a novel and unexpected result. It has also been observed that more than one fluorine can be introduced simultaneously simply by subjecting multiple hydroxylated (e.g. di-, trihydroxy-) vitamin D starting materials to fluorination. Since the fluorination process entails the replacement of free hydroxy function(s) it is essential that any such functions in the starting material that are not to be replaced by fluorine be suitably protected, e.g. by acylation such as acetylation or benzoylation. In particular, a C-3-hydroxy function is present in the starting material, needs to be protected by acylation since, as already mentioned above, treatment of C-3-hydroxyvitamin D compounds or analogs with diethylaminosulfur trifluoride leads to undesired chromophore rearrangement. Protection of hydroxy groups can be accomplished readily by known methods and after fluorination the acyl groups can, of course, be readily removed, if desired, by hydrolysis under basic conditions.

The scope and versatility of the direct fluorination process by which fluorovitamin D compounds of general structure I above, and fluoro-5,6-trans-vitamin D compounds of general structure II above can be prepared from starting materials of general structures III and IV, respectively, is more specifically illustrated by the following typical conversions.

(1) 25-hydroxyvitamin $D_3$ 3-O-Acyl→25-fluorovitamin $D_3$ 3-O-Acyl
(2) 1α,25-dihydroxyvitamin $D_3$ 1,3-di-O-Acyl→25-fluoro-1α-hydroxyvitamin $D_3$ 1,3-di-O-Acyl
(3) 1α,25-dihydroxyvitamin $D_3$ 3-O-Acyl→1,25-difluorovitamin $D_3$ 3-O-Acyl
(4) 1α-hydroxyvitamin $D_3$ 3-O-Acyl→1-fluorovitamin $D_3$ 3-O-Acyl
(5) 1α,25-dihydroxyvitamin $D_3$ 3,25-di-O-Acyl→1-fluoro-25-hydroxy vitamin $D_3$ 3,25-di-O-Acyl
(6) 24,25-dihydroxyvitamin $D_3$ 3,24-di-O-Acyl→25-fluoro-24-hydroxyvitamin $D_3$ 3,24-di-O-Acyl
(7) 1,24,25-trihydroxyvitamin $D_3$ 3,24,25-tri-O-Acyl→1-fluoro-24,25-dihydroxyvitamin $D_3$ 3,24,25-tri-O-Acyl
(8) 3-deoxy-1α-hydroxyvitamin $D_3$→3-deoxy-1-fluorovitamin $D_3$
(9) 3-deoxy-1α,25-dihydroxyvitamin $D_3$→3-deoxy-1,25-diflurovitamin $D_3$
(10) 25-hydroxyvitamin $D_2$ 3-O-Acyl→25-fluorovitamin $D_2$ 3-O-Acyl
(11) 1,25-dihydroxyvitamin $D_2$ 1,3-di-O-Acyl→25-fluoro-1α-hydroxyvitamin $D_2$ 1,3-di-O-Acyl
(12) 1,25-dihydroxyvitamin $D_2$ 3-O-Acyl→1,25-difluorovitamin $D_2$ 3-O-Acyl
(13) 25-hydroxy-5,6-trans-vitamin $D_3$ 3-O-Acyl→25-fluoro-5,6-transvitamin $D_3$ 3-O-Acyl
(14) 1α,25-dihydroxy-5,6-trans-vitamin $D_3$ 3-O-Acyl→1,25-difluoro-5,6-trans-vitamin $D_3$ 3-O-Acyl
(15) 25-hydroxy-5,6-trans-vitamin $D_2$ 3-O-Acyl→25-fluoro-5,6-transvitamin $D_2$ 3-O-Acyl
(16) 1,25-dihydroxy-5,6-trans-vitamin $D_2$ 3,25-di-O-Acyl→1-fluoro-25-hydroxy-5,6-trans-vitamin $D_2$ 3,25-di-O-Acyl
(17) 25,26-dihydroxy-5,6-trans-vitamin $D_3$ 3-O-Acyl→25,26-difluoro-5,6-trans-vitamin $D_3$ 3-O-Acyl It is to be appreciated that the foregoing reactions are meant to be illustrative only. The examples are presented to show that the process provides for the convenient introduction of fluorine into both ring A and the side chain of the steroid molecule, and, specifically that vitamin D compounds and analogs having fluorine substituents at any one or more of carbons 1, 24, 25, or 26 can be readily made from the correspondingly hydroxylated starting materials.

A preferred reagent for fluorination is diethylaminosulfur trifluoride [Middleton, *J. Org. Chem.* 40, 574 (1975)]. The reaction is conveniently conducted in a halo-carbon solvent, such as methylene chloride, carbon tetrachloride or trichlorofluoromethane, at low temperature, e.g. −78° C. For the displacement of hydroxy groups by fluorine, short reaction times, e.g. 15–45 min, are adequate. Although the reagent also attacks keto groups in the molecule, it does so at a much slower rate, and therefore, protection of any keto function present is not normally required under conditions where displacement of hydroxy groups is desired. It is therefore possible to fluorinate keto-vitamin D derivatives directly. For example, 1-oxoprevitamin D compounds are readily side-chain fluorinated as illustrated by reaction 18 below.

(18) 25-hydroxy-1-oxoprevitamin $D_3$ 3-O-Acyl→25-fluoro-1-oxo-previtamin $D_3$ 3-O-Acyl 1-Oxo-previtamin D compounds are readily prepared by the procedure of Paaren et al., *J. Chem. Soc. Chem. Comm.* 890 (1977) and can be converted to both 1α- and 1β-vitamin D compounds by reduction and thermal isomerization as described by Paaren et al. in the above cited reference. Thus the 25-fluoro-1-oxoprevitamin $D_3$ 3-O-Acyl product of the reaction above, after reduction by hydride reducing agents (e.g. LiAlH₄) yields a mixture of 1α-hydroxy-25-fluoroprevitamin $D_3$ and 1β-hydroxy-25-fluoroprevitamin $D_3$, which can be separated by chromatography, and then thermally isomerized using the conditions of Paaren et al. in the above cited reference, to the desired products, 1α-hydroxy-25-fluorovitamin $D_3$ and 1β-hydroxy-25-fluorovitamin $D_3$. Fluorinated 1-oxo-previtamin D compounds, therefore, represent novel and useful intermediates for the synthesis of desired 1-hydroxy-fluorovitamin D compounds.

As mentioned previously, and as illustrated by the reactions above, any hydroxy groups in the starting material that are not to be replaced by fluorine in this process must be protected, e.g. acylated (acetylated, benzoylated). In particular, a hydroxy function at carbon 3 (as is commonly present in vitamin D compounds or analogs) needs to be protected by acylation, since, as mentioned above, fluorination in the presence of a C-3 hydroxy group can lead to undesired products. Acylation of hydroxy groups is, of course, a well-known procedure, and is normally accomplished by treating the hydroxy compound with an acylating agent (e.g. acetic anhydride, benzoyl chloride) in a suitable solvent (e.g. pyridine). Primary and secondary hydroxy groups in vitamin D compounds or their analogs are readily acylated using such reagents and solvents, at room temperature (or slightly elevated temperature, e.g. 50° C.), over a period of 2–6 hr. Acylation of tertiary hydroxy groups requires, of course, more vigorous conditions, e.g. elevated temperatures (e.g. 75°–100° C.), and appropriate reaction times, e.g. 4–24 hr. It is preferably to conduct the reaction under a nitrogen atmosphere to avoid decomposition of material. Selective acylation of specific hydroxyl groups is also readily accomplished. Thus, by way of example, 25-hydroxyvitamin $D_3$ 3-acetate, or 1,25-dihydroxyvitamin $D_3$ 1,3-diacetate (see reactions 1 and 2, where acyl represents acetyl) can be obtained by acetylation of 25-hydroxyvitamin $D_3$ and 1,25-dihydroxyvitamin $D_3$, respectively at room temperature, since under such conditions the tertiary hydroxy group does not react. The acylated starting materials illustrated in reactions 6, 10, 11, 13, and 15 above are obtained similarly. Where selective acylation of chemically similar hydroxy groups is required, chromatographic separation of products may be necessary. Thus, 1α-hydroxyvitamin $D_3$ 3-acetate can be prepared by conducting an acetylation at room temperature and stopping the reaction before complete acetylation has occurred. Under such circumstances, a mixture of four compounds is obtained: 1α-hydroxyvitamin $D_3$, 1α-hydroxyvitamin $D_3$ 1-acetate, 1α-hydroxyvitamin $D_3$ 3-acetate and 1α-hydroxyvitamin $D_3$ 1,3-diacetate, from which the desired product, e.g. 1α-hydroxyvitamin $D_3$ 3-acetate [see reaction (4)] is obtained by chromatography. Other partially acylated products that are required as starting materials for subsequent fluorination (e.g. as in reactions 3, 12, 14) are obtained in the analogous fashion. Alternatively, partially acylated compounds can be obtained by first acylating all hydroxy groups and then removing one or more of the acyl functions by hydrolysis. Thus the 1,25-dihydroxyvitamin $D_3$ 3,25-di-O-acyl compound (reaction 5) can be obtained by partial hydrolysis under basic conditions of the 1,25-dihydroxyvitamin D3 1,3,25-tri-O-acyl derivative. The same 3,25-di-O-acyl derivative can be prepared, if desired, by the following route: acylation of 25-hydroxy-6-methoxy-3,5-cyclo vitamin D3 to produce the 25-O-acyl derivative, selenium dioxide oxidation of that derivative [using the method of Paaren et al., Proc. Nat. Acad. Sci. USA 75, 2080 (1978)] to give the 1α-hydroxy analog, formylation of that derivatives (using formic/acetic anhydride) to give the 1-O-formyl compound, solvolysis of that intermediate in acetic acid to yield 1,25-dihydroxyvitamin D3 3-acetate-25-O-acyl-1-formate and finally hydrolysis of the formate (in dilute Na2CO3, for 10 minutes at room temperature) to produce the desired 3,25-di-O-acyl protected derivative of 1,25-dihydroxyvitamin D3. These examples are cited to show that many different methods are known and available to produce O-protected vitamin D compounds as may be required for the subsequent fluorination reaction.

Once fluorine has been introduced into the molecule, all acyl groups, if present, can be removed by basic hydrolysis, e.g. treatment of the acylated fluoro analog with 5% KOH in MeOH, at a temperature of 25°–80° C. for 1–4 hr. The resulting deacylated fluorinated products are then conveniently further purified by chromatography.

In general, therefore, the overall process for the preparation of fluorovitamin D compounds of general structures I or II from the corresponding starting materials represented by general structures III or IV may involve three basic operations: (a) a preliminary protection step in which the C-3-hydroxy function (if present) and/or any other hydroxy function in the starting material that is not to be replaced by fluorine is acylated; (b) the fluorination step in which fluorine replaces any free hydroxy groups remaining after step (a), and finally, if desired (c) a deprotection step in which the protecting acyl groups introduced in step (a) are removed by hydrolysis under basic conditions. Of course, in those instances where the starting material contains no C-3-hydroxy function, and where all other hydroxy functions present are to be replaced by fluorine (e.g. see reactions 8 and 9 above), only a single fluorination step is required to produce the desired product.

A novel alternative method for the preparation of fluorinated vitamin D compounds involves the use of cyclovitamin D compounds of general structure V above, as starting material. It has been found that fluorination of 3,5-cyclovitamin D compounds of general structure V above is readily accomplished using the methods described previously. Fluorination of cyclovitamin D compounds of structure V represents a general and convenient method for the conversion of C-3-hydroxyvitamin D compounds to both fluorovitamin D compounds and fluoro-5,6-trans-vitamin D compounds represented respectively by general structures I and II above in which $R_1$ is selected from the group consisting of hydroxyl or O-acyl and where R, $R_2$, $R_3$, $R_4$, $R_5$ and $R_6$ represent substituents as previously defined.

These cyclovitamin D derivatives are conveniently prepared from C-3-hydroxyvitamin D compounds by the methods published by Sheves and Mazur [*J. Am. Chem. Soc.* 97, 6249 (1975)] and Paaren et al. [*Proc. Nat. Acad. Sci.* USA 75, 2080 (1978)]. Using the process of the present invention these compounds are readily fluorinated at carbon 1 and/or any of the side chain positions. After fluorine introduction, the fluorocyclovitamin derivatives can be subjected to acid catalyzed solvolysis as described by Sheves and Mazur and Paaren et al. in the above cited references, to yield both fluorovitamin D compounds and 5,6-trans-fluorovitamin D compounds which can be readily separated by chromatography. The reactions below illustrate typical conversions.

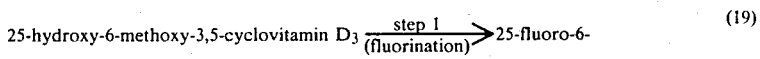
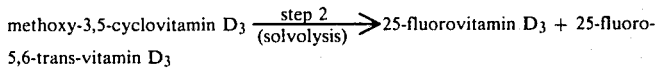

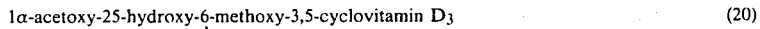
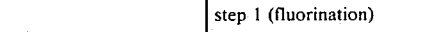
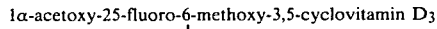
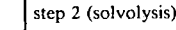
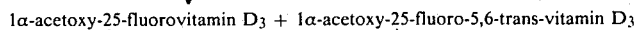
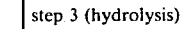
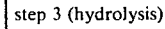
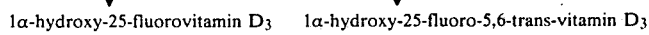

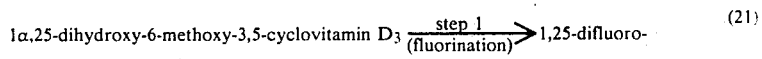
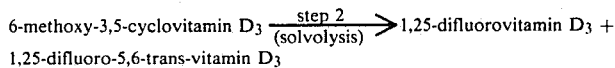

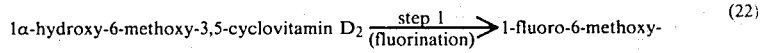
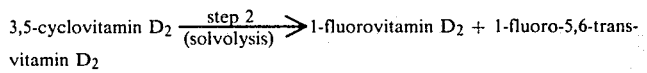

The cyclovitamin starting materials shown in reaction 20–22 above are prepared as described by Paaren et al. in the above cited reference. In any of the illustrated examples, step 1 represents the fluorination reaction using diethylaminosulfur trifluoride as described earlier, and step 2 represents acid catalyzed solvolysis using any of the conditions of Paaren et al., in the above cited reference and step 3 represents hydrolysis of acyl protecting groups (if present).

As shown by the above illustrative reactions, solvolysis yields both the 5,6-cis vitamin D products and the corresponding 5,6-trans vitamin D analogs. These fluorinated cis and trans reaction products can be conveniently separated by chromatography at this stage (as described by Paaren et al. in the above cited reference) and then can be separately subjected to hydrolysis (if acyl protecting groups are to be removed) using the standard conditions described earlier, e.g. 0.1 M KOH in methanol, 60° C., 1-4 hr. Depending upon the exact solvolyzing conditions, 5,6-cis and -trans products with different C-3 substituents are obtained. Thus, conducting the solvolysis in a medium consisting of aqueous dioxane and a catalytic amount of p-toluene sulfonic acid yields fluorinated 5,6-cis and trans products bearing a C-3-hydroxy substituent. Solvolysis of fluorocyclovitamin D compounds in warm acetic acid (e.g. 50°-60° C.) yields 5,6-cis and trans fluorovitamin D compounds bearing a C-3-acetoxy substituent, and if the solvolysis of fluorocyclovitamins in conducted in dioxane/formic acid solvents, the corresponding 3-O-formyl 5,6-cis and trans products are obtained. If desired these C-3-O-acylated products can be readily converted to the corresponding C-3-hydroxy compounds by mild base hydrolysis.

The production of both 5,6-cis and 5,6-trans-fluorovitamin D compounds (which are readily separable by chromatography) is an advantageous feature of this novel process, and it is to be particularly noted that this novel method utilizing cyclovitamin D intermediates permits the introduction of fluorine into either side chain positions and/or at carbon 1 of ring A. These C-1-fluorinated 3,5-cyclovitamin D derivatives are new and highly useful intermediates.

EXAMPLE 1

25-Hydroxyvitamin $D_3$ 3-acetate: To 105 mg 25-hydroxyvitamin $D_3$ dissolved in 1.3 ml dry pyridine is added 110 mg acetic anhydride. After heating at 50° C. under nitrogen for 5 hr, volatiles are removed by rotary evaporation. The resulting oil is dissolved in 15 ml of ethyl acetate then washed with an equal volume of 5% HCl, followed by 5% NaHCO$_3$, and finally saturated brine. After drying (Na$_2$SO$_4$), the solution is applied to a silica gel thin layer plate. Development with 20% ethyl acetate in Skellysolve B and elution of the major band with ethyl acetate gives 92.5 mg (79%) of monoacetate, i.e. 25-hydroxyvitamin $D_3$ 3-acetate, as a colorless oil: uv (EtOH) $\lambda_{max}$ 265 nm ($\epsilon$15,000); ir (CCl$_4$) 3620 (hydroxyl), 3080 (exocyclic methylene), 1735 and 1242 cm$^{-1}$ (acetate); nmr (CDCl$_3$) $\delta$6.22 (d, J=11 Hz, 1H, C-6), 6.03 (d, J=11 Hz, 1H, C-7), 5.06 (d of t, $J_1$=2.2 Hz, $J_2$=1.1 Hz, 1H, C-19), 4.94 (t of t, $J_1$=4 Hz, $J_2$=8.1 Hz, 1H, C-3), 4.84 (d, J=2.2 Hz, 1H, C-19), 2.04 (s, 3H, acetate), 1.21 (s, 6H, C-26,27), 0.93 (d, J=5.4 Hz, 3H, C-21), 0.54 (s, 3H, C-18); mass spectrum m/e (relative intensity) 442.3421 (57, M$^+$, 442.3447 calcd. for C$_{29}$H$_{46}$O$_3$), 382 (82), 367 (30), 253 (30), 158 (77), 118 (100), 59 (75); homogeneous on tlc (R$_f$=0.43, 20% ethyl acetate in Skellysolve B).

EXAMPLE 2

25-Fluorovitamin $D_3$ 3-acetate: A solution of 25-hydroxyvitamin $D_3$ 3-acetate (15 mg) in 0.5 ml of dichloromethane is added dropwise to a cooled (Dry Ice/2-propanol) mixture of diethylaminosulfur trifluoride (30 mg) in 0.5 ml of dichloromethane. After stirring 5 min the cooling bath is removed and the contents are warmed to ambient temperature (15 min). Five ml 4% aqueous NaHCO$_3$ and 10 ml dichloromethane are added. The organic phase is separated, washed with water, dried (Na$_2$SO$_4$), and solvents are removed by flash evaporation. This provides a yellow oil that is applied to a silica gel preparative tlc plate. After developing with 10% ethyl acetate in Skellysolve B, the major product is eluted with ethyl acetate. Solvent removal gives tertiary fluoride, 25-fluorovitamin $D_3$ 3-acetate (9.0 mg, 59%) as a colorless oil: uv (EtOH) $\lambda_{max}$ 265 nm ($\epsilon$16,000); ir (CCl$_4$) 3080 (exocyclic methylene), 1740 and 1240 cm$^{-1}$ (acetate); nmr (CDCl$_3$) $\delta$6.21 (d, J=11 Hz, 1H, C-6), 6.03 (d, J=11 Hz, 1H, C-7), 5.06 (m, 1H, C-19), 4.94 (t of t, $J_1$=9 Hz, $J_2$=4 Hz, 1H, C-3), 4.83 (d, J=2.2 Hz, 1H, C-19), 2.04 (s, 3H, acetate), 1.34 (d, $J_{HF}$=21.7 Hz, 1H, C-26,27), 0.93 (d, J=6 Hz, 3H, C-21), 0.54 (s, 3H, C-18); mass spectrum m/e (relative intensity) 444.3385 (12, M$^+$, 444.3404 calcd. for C$_{29}$H$_{45}$O$_2$F) 384 (58), 369 (10), 364 (6), 253 (22), 158 (44), 118 (100), 61 (22), 59 (1); homogeneous on tlc (R$_f$=0.56, 10% ethyl acetate in Skellysolve B).

EXAMPLE 3

25-Fluorovitamin $D_3$: 25-Fluorovitamin $D_3$ 3-acetate (7.5 mg) is dissolved in 20 ml of 1.0 M KOH in methanol. After stirring at room temperature for 35 min, 5 ml water and 10 ml chloroform are added. The phases are separated; the aqueous phase is extracted twice with chloroform (5 ml each); the organic phases are combined then washed with dilute acid followed by saturated brine. After drying (Na$_2$SO$_4$), the solution is applied to a silica tlc plate. Development with 20% ethyl acetate in Skellysolve B and elution of the predominant product with ethyl acetate provides 4.9 mg (72%) of the desired 25-fluorovitamin $D_3$ as a colorless oil: uv (EtOH) $\lambda_{max}$ 265 nm; ir (CCl$_4$) 3620 (hydroxyl), 3080 cm$^{-1}$ (exocyclic methylene); nmr (CDCl$_3$) $\delta$6.24 (d, J=11 Hz, 1H, C-6), 6.03 (d, J=11 Hz, 1H, C-7), 5.05 (m, 1H, C-19), 4.82 (d, J=2.6 Hz, 1H, C-19), 3.95 (t of t, $J_1$=7.1 Hz, $J_2$=3.6 Hz, 1H, C-3), 1.34 (d, $J_{HF}$-21.3 Hz, 6H, C-26,27), 0.93 (d, J=6 Hz, 3H, C-21), 0.54 (s, 3H, C-18); mass spectrum m/e (relative intensity) 402.3284 (13, M$^+$, 402.3298 calcd. for C$_{27}$H$_{43}$OF), 360 (4), 271 (4), 253 (5), 136 (100), 118 (88), 61 (12), 59 (1); homogeneous on tlc (R$_f$=3.6 and 3.9 min for the pyro and isopyro derivatives, 2 mm×6' 3% OV101, 260° oven isothermal).

EXAMPLE 4

1$\alpha$-Hydroxyvitamin $D_3$ 3-acetate: 1$\alpha$-Hydroxyvitamin $D_3$ (25 mg, 0.063 mmole) and acetic anhydride (50 $\mu$l) in pyridine-benzene (2 ml, 1:1) are heated at 50° C. under argon for 4 hr. The reaction mixture is cooled, water and ether are added, and the phases are separated. The ether layer is washed with water, 1 N HCl (2 times), dilute NaHCO$_3$, saturated NaCl and dried (Na$_2$SO$_4$). The solvent is evaporated and the residue is chromatographed on a silica gel plate (20×20 cm, 0.75 cm thick) developed with ethyl acetate/Skellysolve B (1:1). Four bands of R$_f$ 0.20, 0.38, 0.49 and 0.64 are apparent. The band with $R_f$ 0.49 consists of product, 1α-hydroxyvitamin $D_3$ 3-acetate, 6.0 mg (22%).

The bands with $R_f$ 0.64, 0.38, and 0.20 consist of 1α-hydroxyvitamin $D_3$ 1,3-diacetate, 1α-hydroxyvitamin $D_3$ 1-acetate, and starting material (7.3 mg, 29%), respectively. The undesired 1-acetate and the diacetate are combined (6.8 mg, 23–25%), hydrolyzed (1 ml 0.1 M KOH/MeOH; 1 ml ether, 1.25 hr, room temperature), and pooled with starting material to give 14 mg 1α-hydroxyvitamin $D_3$. This process is repeated twice more to give a total of 12 mg (43%) 1α-hydroxyvitamin $D_3$ 3-acetate: uv (95% EtOH) $\lambda_{max}$ 265, $\lambda_{min}$ 228; nmr (270 MHz, $CDCl_3$) δ0.54 (s, 18-$CH_3$), 0.87 (d, J=6.6 Hz, 26,27-$(CH_3)_2$), 0.92 (d, J=6.1 Hz, 21-$CH_3$), 2.03 (s, 3 AcO-), 4.41 (m, 1β-H), 5.02, 5.34 (19-H's), 5.34 (3α-H), 6.02, 6.34 (AB quartet, J=11.4 Hz, 6 and 7-H's).

EXAMPLE 5

1-Fluorovitamin $D_3$: To 2 mg 1α-hydroxyvitamin $D_3$ 3β-acetate in $CH_2Cl_2$ (0.4 ml) at $-78°$ C. is added DAST (12 μl) with good stirring. The cooling bath is removed and 5 min later the reaction is quenched with 5% $K_2CO_3$. Ether is added and the phases are separated. The organic phase is washed with water, and brine, and concentrated to 0.5 ml. To the organic phase 0.1 M KOH/MeOH (1 ml) is added. After 1.5 hr at room temperature the solvent is removed, ether and water are added, the phases are separated. The ether phase is washed with water and brine and filtered through $Na_2SO_4$. The residue obtained after evaporation of the ether is chromatographed over a microparticulate silica gel column (5μ particles, 0.7×25 cm) eluted with 0.5% isopropanol/hexane. The desired product elutes in 78 ml (0.85 mg): uv $\lambda_{max}$ 265, $\lambda_{min}$ 226 nm, $\lambda_{max}/\lambda_{min}$ 2.1; nmr (benzene-$d_6$) δ0.63 (s, C-18 methyl), 0.98 (d, J=6.1 Hz, C-26,27 methyls), 1.01 (d, J=6.5 Hz, C-21 methyl), 3.52 (m, $w_{\frac{1}{2}}$ 24 Hz, 3α-proton), 4.71 (doublet of multiplets, J=50 Hz, $w_{\frac{1}{2}}$ 20 Hz), 5.23 5.55 (two s, 19-protons), 6.38, 6.52 (AB q, J=11 Hz, 6- and 7-protons); mass spectrum m/e (relative intensity) 402.3320 ($M^+$, 0.10, calcd. for $C_{27}H_{43}FO$, 402.3298), 382 ($M^+$-HF, 0.40), 364 ($M^+$-HF-$H_2O$, 0.28), 349 ($M^+$-HF-$H_2O$, 0.28), 349 ($M^+$-HF-$H_2O$-$CH_3$, 0.04), 289 ($M^+$-side chain, 0.05), 269 ($M^+$-side chain-HF, 0.08), 251 ($M^+$-side chain-HF-$H_2O$, 0.10), 135 (1.00).

EXAMPLE 6

1α,25-Dihydroxyvitamin $D_3$ 3-acetate: 1α,25-Dihydroxyvitamin $D_3$ (25 mg) and acetic anhydride (50 μl) in pyridine-benzene (2 ml, 1:1) are heated at 50° C. under argon for 4 hr. The usual work-up gives a mixture of partially acetylated products (including the 1-acetate, the 3-acetate and the 1,3-diacetate) from which the desired 3-acetate product is separated by preparative-layer chromatography on silica gel developed with 40% ethyl acetate in Skellysolve B. Recycling of the unreacted starting material and hydrolysis of undesired 1,3-diacetate and 1-acetate improves the overall yield.

EXAMPLE 7

1,25-Difluorovitamin $D_3$: 1α,25-Dihydroxyvitamin $D_3$ 3-acetate (3 mg) in $CH_2Cl_2$ at $-78°$ C. under argon is treated with diethylaminosulfur trifluoride (20 μl). The solution is allowed to warm to room temperature and quenched with 5% $K_2CO_3$. Work-up of the reaction is done as described in Example 5. Chromatography of the recovered material over a silica gel plate developed with 25% ethyl acetate in Skellysolve B yields purified, 1,25-difluorovitamin $D_3$ 3-acetate. Hydrolysis (1 ml of 0.1 M KOH/MeOH, 1 ml ether, room temperature, 2 hr) and rechromatography over silica gel (ethyl acetate/Skellysolve B) gives 1,25-difluorovitamin $D_3$.

EXAMPLE 8

1α,25-Dihydroxyvitamin $D_3$ 1,3-diacetate: 1α,25-Dihydroxyvitamin $D_3$ (9.4 mg, 0.022 mmol) is heated at 50° C. for 6 hr under argon with acetic anhydride (0.05 ml) and pyridine (0.3 ml) in benzene (0.3 ml). The reaction mixture is cooled, ether and water are added and the organic phase is separated, and washed with 1 N HCl, 5% $K_2CO_3$, water and brine. TLC (silica, 60% ethyl acetate/hexane) indicated the presence of one compound ($R_f$=0.48), the desired 1,3-diacetate of 1α,25-dihydroxyvitamin $D_3$.

EXAMPLE 9

1α-Hydroxy-25-fluorovitamin $D_3$: Diethylaminosulfur trifluoride (10 μl) is added to a solution of 1α,25-dihydroxyvitamin $D_3$ 1,3-diacetate (0.9 mg, 1.8 mmol) in carbon tetrachloride (0.5 ml) at 10° C. After 10 min, the reaction is quenched with 5% $K_2CO_3$, and chloroform is added. The organic phase is separated, washed with water and dryed ($Na_2SO_4$). The residue obtained after evaporation of the organic phase is dissolved in ether (0.5 ml) and 0.1 M methanolic KOH, and is allowed to stand at room temperature for 1 hr. Ether and water are then added; the phases are separated and the organic phase is washed with water and brine. The residue is chromatographed on a high-pressure liquid chromatograph with 5% isopropanol/hexane to give 86 μg of pure 1α-hydroxy-25-fluorovitamin $D_3$: uv 265 nm ($\epsilon$=18,200); nmr (270 MHz) 0.55 (s, 18-$CH_3$), 0.94 (d, J=6 Hz, 21-$CH_3$), 1.34 (d, J=22 Hz, 26,27-$(CH_3)_2$), 4.23 (m, 3α-H), 4.43 (m, 1β-H), 5.33, 5.01 (2 m, 19-$CH_3$), 5.85, 6.38 (AB quartet, J=11 Hz, 6 and 7-H's); mass spectrum m/e 418.3197 ($M^+$, 0.07, $C_{27}H_{44}O_2F$ calcd. 418.3222), 400.3141 ($M^+$-$H_2O$, 0.22, calcd. 400.3143), 382.3027 ($M^+$-2×$H_2O$, 0.23, calcd. 382.3031), 380.3059 ($M^+$-$H_2O$-HF, 0.18, calcd. 380.3069), 362.2974 ($M^+$-2×$H_2O$-HF, 0.18, calcd. 362.2997), 152.0842 (0.42, calcd. 152.0840), 134.0736 (1.00 calcd. 134.0734).

EXAMPLE 10

24(R)-Hydroxy-25-fluorovitamin $D_3$: 24(R),25-dihydroxyvitamin $D_3$ (5.0 mg) is acetylated with acetic anhydride (100 μl) and pyridine (200 μl) for 1 hr at 50° C. under argon. The reaction mixture is diluted with ether (10 ml) and washed with 1 N HCl, 5% $NaHCO_3$, water, and brine (5 ml each), and dried ($Na_2SO_4$). Evaporation of the organic phase gives 24(R),25-dihydroxyvitamin $D_3$ 3,24-diacetate (5.4 mg); tlc (75% ethyl acetate/hexane) $R_f$ 0.56 ($F_f$ 0.37); uv $\lambda_{max}$ 265 nm, $\lambda_{max}/\lambda_{min}$ 1.8.

The diacetate is immediately fluorinated with 50 μl diethylaminosulfur trifluoride in 400 μl methylene chloride at $-78°$ C. for 2 min. The reaction is quenched by addition of 5% $NaHCO_3$. The mixture is extracted with ether and treated with 0.1 M KOH/methanol for 1.5 hr at room temperature. The solvent is evaporated and water is added to the residue. Extraction of the aqueous mixture with ether and evaporation of the organic phases yields 3.9 mg of crude products. When the mixture is subjected to high-pressure liquid chromatography (0.7×25 cm, 5μ silica gel) and eluted with 2% isopropanol/hexane, three main products are obtained. The second, eluting at 58 ml is 24(R)-hydroxy-25- fluorovitamin $D_3$ (831 μg): uv $\lambda_{max}$ 265 nm; nmr δ0.55 (singlet, 18-methyl), 0.94 (doublet, J=5.9 Hz, 21-methyl), 1.34, 1.33 (two doublets, J=22 Hz each, 26- and 27-methyl), 3.52 (multiplet, 24S-proton), 3.95 (multiplet, 3α-proton), 4.82, 5.06 (multiplets, 19-protons), 6.04, 6.24 (AB quartet, J=12 Hz, 6,7-protons); mass spectrum m/e (composition, m/e calcd.) 418.3264 ($C_{27}H_{43}O_2F$, 418.3247), 398.3132 ($C_{27}H_{42}O_2$, 398.3185), 385.2904 ($C_{26}H_{38}OF$, 385.2906), 271.2050 ($C_{19}H_{27}O$, 271.2061), 253.1962 ($C_{19}H_{25}$, 253.1956), 136.0891 ($C_9H_{12}O$, 136.0888), 118.0783 ($C_9H_{10}$, 118.0782).

The product eluting at 40 ml is 24(R),25-dihydroxyvitamin $D_3$ 24-acetate (533 μg). The compound eluting at 89 ml is 24(R)-hydroxy-25-dehydrovitamin $D_3$ (385 μg).

EXAMPLE 11

25-Fluorovitamin $D_2$-3-acetate: A solution of 2.5 mg of 25-hydroxyvitamin $D_2$ 3-acetate (prepared from 25-hydroxyvitamin $D_2$ and acetic anhydride/pyridine, 50° C., 5 hr, $N_2$) in 0.5 ml of dichloromethane is added to an excess of cold (−78° C.) diethylaminosulfur trifluoride dissolved in the same solvent. The cooling bath is removed, and the contents are allowed to warm to room temperature, at which time excess reagent is destroyed with 4% $NaHCO_3$. The usual work-up gives an oil which is purified on a preparative tlc plate made of silica gel. Development with 10% ethyl acetate in Skellysolve B, and elution of the major band with ethyl acetate gives 25-fluorovitamin $D_2$ 3-acetate exhibiting the expected uv, nmr, and mass spectra.

EXAMPLE 12

25-Fluorovitamin $D_2$: 25-Fluorovitamin $D_2$ 3-acetate (0.5 mg) is dissolved in 0.1 M methanolic KOH and kept at 25° C. for 1 hr. The reaction mixture is diluted with water, then $CHCl_3$ is added and the separated organic phase is evaporated. The resulting oil is purified by silica gel preparative tlc. The plate is developed with 20% ethyl acetate in Skellysolve B and the major band is eluted with ethyl acetate. This gives the desired product, 25-fluorovitamin $D_2$ in good yield and purity.

EXAMPLE 13

1α-Hydroxy-25-fluorovitamin $D_2$: 1α,25-Dihydroxyvitamin $D_2$ is acetylated in acetic anhydride and pyridine (4 hr, 50° C., $N_2$ atmosphere) to give 1α,25-dihydroxyvitamin $D_2$ 1,3-diacetate. A methylene chloride solution of this material is then fluorinated exactly as described in Example 11. The product is isolated as described in Example 11 and purified by thin-layer chromatography (silica gel, 10% ethyl acetate in Skellysolve B as solvent), to give 1α-hydroxy-25-fluorovitamin $D_2$ 1,3-diacetate. Hydrolysis of this product exactly as described in Example 12 gives the desired product 1α-hydroxy-25-fluorovitamin $D_2$.

EXAMPLE 14

25-Fluoro-1-oxoprevitamin $D_3$ 3-acetate: Oxidation of 1α,25-dihydroxyvitamin $D_3$ as described by Paaren et al. [J. Chem. Soc. Chem. Commun. 890, (1977)] yields 1-oxo-25-hydroxyprevitamin $D_3$. This material is acetylated by treatment with acetic anhydride in pyridine (5 hr, room temperature) to yield 1-oxo-25-hydroxyprevitamin $D_3$ 3-acetate. Fluorination of this intermediate as described in Example 11 yields 25-fluoro-1-oxoprevitamin $D_3$ 3-acetate which is purified by preparative thin-layer chromatography using 10% ethyl acetate and Skellysolve B as eluting solvent.

EXAMPLE 15

1,25-Dihydroxyvitamin $D_3$ 25-acetate: A solution of 10 mg of 1,25-dihydroxyvitamin $D_3$ is heated at 90° C. for 16 hr under argon with 0.5 ml of acetic anhydride and 2 ml of pyridine. The usual work-up gives a mixture from which 1,25-dihydroxyvitamin $D_3$ 1,3,25-triacetate (9.5 mg) is separated by chromatography over a preparative layer of silica gel developed with 25% ethyl acetate/Skellysolve B or by high-pressure liquid chromatography with a silica gel column eluted with mixtures of 0.5% 2-propanol in hexane. Selective hydrolysis (0.1 M KOH/MeOH, ether, 1.5 hr, 25° C.) of the 1 and 3 acetates gives 7 mg of 1,25-dihydroxyvitamin $D_3$ 25-acetate, which is purified by chromatography on silica gel thin layer plates using 50% ethyl acetate in Skellysolve B as solvent.

EXAMPLE 16

1,25-Dihydroxyvitamin $D_3$ 3,25-diacetate: 1,25-Dihydroxyvitamin $D_3$ 25-acetate (7 mg) is acetylated using the conditions described in Example 4. From the product mixture 1,25-dihydroxyvitamin $D_3$ 3,25-diacetate (4 mg) is isolated by silica gel thin layer chromatography using ethyl acetate/Skellysolve B (1:1) as solvent system.

EXAMPLE 17

1-Fluoro-25-hydroxyvitamin $D_3$: 1,25-Dihydroxyvitamin $D_3$ 3,25-diacetate (2 mg) in $CHCl_2$ at −78° C. under argon is treated with diethylaminosulfur trifluoride (4 mg). The reaction mixture is allowed to warm to room temperature and quenched with 5% $K_2CO_3$. Chromatography of the recovered material over silica gel high-pressure liquid chromatography eluted with 1% 2-propanol in hexane gives 0.7 mg of 1-fluoro-25-hydroxyvitamin $D_3$ 3,25-diacetate. Hydrolysis (0.1 M KOH/MeOH, ether) and rechromatography over silica gel high-pressure liquid chromatography developed with 5% 2-propanol/hexane yields 1-fluoro-25-hydroxyvitamin $D_3$ in pure form.

EXAMPLE 18

25-Fluoro-5,6-trans-vitamin $D_3$: A 5 mg sample of 25-hydroxy-5,6-trans-vitamin $D_3$ [Holick et al., Biochemistry 11, 2715 (1972)] is acetylated using the conditions described in Example 1 to yield 5.2 mg of 25-hydroxyvitamin $D_3$ 3-acetate. This product is dissolved in $CH_2Cl_2$ at −78° C. under argon and treated with diethylaminosulfur trifluoride (30 μl). The reaction is allowed to warm to room temperature and quenched with 5% $K_2CO_3$. After the usual work-up, (see Example 2) the recovered material is chromatographed by high-pressure liquid chromatography over a silica gel column eluted with 0.5% of 2-propanol in hexane. Hydrolysis of the acetate (0.1 M KOH/MeOH, ether, 2 hr, 40° C.) gives 25-fluoro-5,6-trans-vitamin $D_3$ which is purified by high-pressure liquid chromatography over a silica gel column eluted with 1% 2-propanol in hexane.

EXAMPLE 19

1-Fluoro-25-hydroxy-5,6-trans-vitamin $D_3$: A solution of 2 mg of 1α,25-dihydroxyvitamin $D_3$ 3,25-diacetate in 2 ml of ether containing a drop of pyridine is treated with 0.1 ml of a solution of iodine in Skellysolve B (0.5 mg/ml) and stirred for 15 minutes. After addition of 1 ml of an aqueous solution of sodium thiosulfate, the organic phase is separated, and solvent is evaporated. The desired product, $1\alpha,25$-dihydroxy-5,6-transvitamin $D_3$ 3,25-diacetate is isolated by thin layer chromatography on silica gel using 20% ethyl acetate in Skellysolve B as solvent system, (yield 0.8 mg). This material is directly fluorinated using the conditions described in Example 5 ($CH_2Cl_2$ solution, 10 $\mu$l diethylaminosulfur trifluoride, $-78°$ C.) and after work-up as described in Example 5, the recovered product is hydrolyzed (0.1 M KOH, MeOH/ether, 60° C., 3 hr). Purification of the hydrolysis product by high-pressure liquid chromatography on silica gel columns using 3% 2-propanol in Skellysolve B as solvent yields 200 $\mu$g of 1-fluoro-25-hydroxy-5,6-trans-vitamin $D_3$.

EXAMPLE 20

$1\alpha$-Hydroxy-25-fluoro-5,6-trans-vitamin $D_3$: A solution of 5 mg of $1\alpha,25$-dihydroxyvitamin $D_3$ 1,3-diacetate in 2 ml of ether containing 2 drops of pyridine is treated with 0.2 ml of a solution of iodine in Skellysolve B (0.5 mg/ml) and stirred for 15 min. After a work-up of the reaction as described in Example 19, the desired $1\alpha,25$-dihydroxy-5,6-trans-vitamin $D_3$ 1,3-diacetate is purified by thin layer chromatography (silica gel plates, 10% ethyl acetate in Skellysolve B) to yield 2 mg of product. This product is fluorinated using the conditions of Example 9 ($CH_2Cl_2$ solution, 15 $\mu$l of diethylaminosulfur trifluoride, $-78°$ C., 15 min) and after work-up as in Example 5, the product is hydrolyzed (0.1 M KOH in MeOH/ether, 25° C., 1.5 hr). The hydrolysis mixture is diluted with water, and the product is extracted into ether. Purification by high-pressure liquid chromatography (silica gel column, 5% 2-propanol in hexane as solvent) gives 300 $\mu$g of $1\alpha$-hydroxy-25-fluoro-5,6-trans-vitamin $D_3$.

EXAMPLE 21

$1\alpha,25$-Difluoro-6-methoxy-3,5-cyclovitamin $D_3$: A solution of 1 mg of 1,25-dihydroxy-6-methoxy-3,5-cyclovitamin $D_3$ [prepared by the method of Paaren et al. Proc. Nat. Acad. Sci. USA, 75, 2080 (1978)] in $CH_2Cl_2$ at $-78°$ C. under argon is treated with diethylaminosulfur trifluoride (2 mg). After 10 minutes, the reaction mixture is allowed to warm to room temperature and quenched with 5% $K_2CO_3$. After the usual work-up, (e.g. see Example 5) 1,25-difluoro-6-methoxy-3,5-cyclovitamin $D_3$ (250 $\mu$g) is isolated in pure form by high-pressure liquid chromatography using a silica gel column eluted with 10% tetrahydrofuran/hexane. Alternatively, the product can be purified by thin-layer chromatography on silica gel using 20% ethyl acetate in Skellysolve B as developing solvent.

EXAMPLE 22

$1\alpha,25$-Dihydroxy-6-methoxy-3,5-cyclovitamin $D_3$ 1-acetate: 1,25-Dihydroxy-6-methoxy-3,5-cyclovitamin $D_3$ (5 mg) prepared by the method of Paaren et al. [Proc. Nat. Acad. Sci. USA, 75, 2080 (1978)] is acetylated with acetic anhydride (0.5 ml) and pyridine (2 ml) at 50° C. under argon for 2 hr. After the usual work-up, the 1-acetate product (5.5 mg) is isolated by high-pressure liquid chromatography over a silica gel column eluted with 2% 2-propanol/hexane.

EXAMPLE 23

25-Fluoro-$1\alpha$-hydroxy-6-methoxy-3,5-cyclovitamin $D_3$ 1-acetate: 1,25-Dihydroxy-6-methoxy-3,5-cyclovitamin $D_3$ 1-acetate (3 mg) in $CH_2Cl_2$ at $-78°$ C. under argon is treated with diethylaminosulfur trifluoride (5 mg). After several minutes, the reaction mixture is allowed to warm to room temperature and quenched with 5% $K_2CO_3$. Additional $CH_2Cl_2$ is added, the organic phase is separated and the 25-fluorinated product is isolated by thin-layer chromatography using a silica gel plate and 20% ethyl acetate in hexane as solvent, to yield 2 mg of pure product.

EXAMPLE 24

25-Fluoro-$1\alpha$-hydroxy-6-methoxy-3,5-cyclovitamin $D_3$: A sample of 25-fluoro-cyclovitamin derivative as obtained in Example 23 is dissolved in 0.1 M KOH/methanol solvent and warmed to 50° C. for 2 hrs. Water is then added and the hydrolyzed product is extracted into ether. Purification by thin-layer chromtography on silica gel plates developed with 30% ethyl acetate in Skellysolve B yields pure 25-fluoro-1-hydroxy-6-methoxy-3,5-cyclovitamin $D_3$.

EXAMPLE 25

1-Fluoro-6-methoxy-3,5-cyclovitamin $D_2$: A methylene chloride solution of 10 mg $1\alpha$-hydroxy-6-methoxy-3,5-cyclovitamin $D_2$ [prepared as described by Paaren et al. Proc. Nat. Acad. Sci. USA 75, 2080 (1978)] is cooled to $-78°$ C. and treated with 20 mg of diethylamino sulfur trifluoride. After 15 minutes the solution is warmed to room temperature, aqueous $NaHCO_3$ (5 ml) and $CH_2Cl_2$ (10 ml) are added. The organic phase is separated, solvent is evaporated and the product is purified by preparative thin-layer chromatography (silica gel plates), 10% ethyl acetate in Skellysolve B as developing solvent, to yield 1-fluoro-6-methoxy-3,5-cyclovitamin $D_2$.

EXAMPLE 26

25-Fluoro-$1\alpha$-hydroxyvitamin $D_3$ and 25-fluoro-$1\alpha$-hydroxy-5,6-trans-vitamin $D_3$: A solution of 3 mg of 25-fluoro-$1\alpha$-acetoxy-6-methoxy-3,5-cyclovitamin $D_3$ [the product of Example 23] is a 3:1 mixture of dioxane and water (1.5 ml) containing 0.2 mg of P-toluenesulfonic acid is warmed to 55° for 15 min. Saturated $NaHCO_3$ (2 ml) is then added and the products are extracted into ether. The ether solvent is dried and evaporated and the residue is chromatographed on silica gel plates to separate the 5,6-cis and 5,6-trans 25-fluorovitamin D products. Development with 25% ethyl acetate in Skellysolve B gives 1 mg of pure 25-fluoro-$1\alpha$-acetoxyvitamin $D_3$ and 0.3 mg of 25-fluoro-$1\alpha$-acetoxy-5,6-trans vitamin $D_3$. Hydrolysis of 25-fluoro-$1\alpha$-acetoxy vitamin $D_3$ in 0.1 M KOH/MeOH, for 2 hrs. at 50° gives a single product, 25-fluoro-$1\alpha$-hydroxyvitamin $D_3$. Similar hydrolysis of 25-fluoro-$1\alpha$-acetoxy-5,6-transvitamin $D_3$ yields 25-fluoro-$1\alpha$-hydroxy-5,6-trans vitamin $D_3$ in pure form.

EXAMPLE 27

1-Fluorovitamin $D_2$ and 1-Fluoro-5,6-trans-vitamin $D_2$: A solution of 3 mg of 1-fluoro-6-methoxy-3,5-cyclovitamin $D_2$ [see Example 25] is dry dioxane (2 m is warmed to 55° and treated with a 1:1 mixture of 98% formic acid:dioxane (150 $\mu$l). After 15 min., ice-water added and the products are extracted with ether. The solvent is evaporated and the product mixture (consisting of 1-fluorovitamin $D_2$ 3-formate and 1-fluoro-5,6-trans-vitamin $D_2$ 3-formate) is directly hydrolyzed by dissolution in dioxane:methanol (1:1) and treatment with aqueous $K_2CO_3$ solution (10 mg/0.1 ml). Hydrolysis is complete after 5 min. at room temperature, and the solution is diluted with water and the products extracted into ether. Chromatography on silica gel plates (750μ thick) using 1:3 ethyl acetate:Skellysolve B as eluting solvent, separates the 5,6-cis, and 5,6-trans products and yields pure 1-fluorovitamin $D_2$ (1 mg) and 1-fluoro-5,6-trans-vitamin $D_2$ (0.3 mg).

EXAMPLE 28

1α,24(R)25-trihydroxy-6-methoxy-3,5-cyclovitamin $D_3$ 1,24-diacetate: A pyridine solution (0.2 ml) of 10 mg of 24(R)25-dihydroxyvitamin $D_3$ is treated with 1.5 eg. of p-toluene sulfonyl chloride at 0° for 48 hr. Dilution with saturated $NaHCO_3$ solution, and extraction with ether yields crude 3-tosyl product. This product in 2 ml MeOH is treated wtih 25 mg of $NaHCO_3$ and heated under $N_2$ at 50° for 20 hr. Dilution with water and extraction with ether gives the cyclovitamin product. Chromatography of the product on silica gel plates (40% ethyl acetate in Skellysolve B) gives 4 mg of 24(R),25-dihydroxy-6-methoxy-3,5-cyclovitamin $D_3$ in pure form.

This product is oxidized by treatment with $SeO_2$ according to the procedures of Paaren et al. Proc. Nat. Acad. Sci. USA 75, 2080 (1978): 4 mg of the cyclovitamin in $CH_2Cl_2$ solution (0.5 ml) is treated with $SeO_2$ (1 mg) and 10 μl of 70% t-butylhydroperoxide, for 30 min. at 25°. After addition of NaOH solution (10%), the 1-hydroxycyclovitamin product is extracted into ether. Evaporation of solvent gives an oil which is chromatographed on silica gel plates using 50% ethyl acetate in Skellysolve B, to yield 1.5 mg of 1α,24(R),25-trihydroxy-6-methoxy-3,5-cyclovitamin $D_3$. This product is acetylated under the usual conditions (0.2 ml of acetic anhydride in in 1 ml pyridine, 50°, 2 hr). Dilution of the reaction mixture with water, extraction with ether, and evaporation of the ether yields ca. 2 mg of 1α,24(R),25-trihydroxy-6-methoxy-3,5-cyclovitamin $D_3$ 1,24-diacetate, sufficiently pure for subsequent fluorination.

EXAMPLE 29

25-fluoro-1,24(R)-dihydroxy-6-methoxy-3,5-cyclovitamin $D_3$ 1,24-diacetate: The diacetoxycyclovitamin product obtained in Example 28 is fluorinated under the usual conditions ($CH_2Cl_2$ solvent, 3 mg of diethylaminosulfur trifluoride, −78°, 15 min.). The reaction mixture is then allowed to warm to room temperature, quenched with 5% $K_2CO_3$ solution and additional $CH_2Cl_2$ is added. The organic phase is separated and the 25-fluorinated product is isolated and purified by thin-layer chromatography on silica gel plates using 25% ethyl acetate in Skellysolve B as solvent system to yield 1 mg of 25-fluoro-1α,24(R)dihydroxy-6-methoxy-3,5-cyclovitamin $D_3$ 1,24-diacetate.

EXAMPLE 30

25-fluoro-1α,24(R)-dihydroxyvitamin $D_3$ and 25-fluoro-1α,24(R)-dihydroxy-5,6-trans-vitamin $D_3$: A dioxane solution of the 25-fluoro cyclovitamin product was obtained in Example 29 is warmed to 55° and treated with a 1:1 mixture of dioxane: 98% formic acid (200 μl). After 15 min. ice-water is added and the products are extracted with ether. After evaporation of solvent, the residue is taken up in dioxane/methanol (1:1, 1 ml) and treated 0.1 ml of an aqueous $K_2CO_3$ solution for 5 min. (to hydrolyze the C-3-formate groups). Extraction of the products into ether, and chromatography on silica gel plates (using 40% ethyl acetate in Skellysolve B) yields 0.3 mg of 25-fluoro-1α,24(R)-dihydroxyvitamin $D_3$ 1,24-diacetate and 0.1 mg of 25-fluoro-1α,24(R)-dihydroxy-5,6-trans-vitamin $D_3$ 1,24-diacetate. The former product is hydrolyzed (0.1 M KOH/MeOH, 50°, 3 hr.) to 25-fluoro-1α,24(R)-dihydroxyvitamin $D_3$. Similar hydrolysis of the 5,6-trans-diacetate yields 25-fluoro-1α,24(R)-dihydroxy-5,6-trans-vitamin $D_3$.

Biological activity of fluorovitamin D compounds

The novel fluorovitamin D compounds prepared as described above exhibit significant vitamin D-like biological activity when tested in vitamin D-deficient animals. The vitamin D-like activities exhibited by these fluorovitamin D compounds include the stimulation of intestinal calcium transport, the stimulation of calcium mobilization from bone and the calcification of bone. For the demonstration of these effects a desirable test animal is the male weanling rat maintained on a vitamin D-deficient low calcium diet, or a vitamin D-deficient, low-phosphorus diet, as described by Suda et al. J. Nutr. 100, 1049 (1970). With animals maintained on a low calcium diet, intestinal calcium absorption can be assayed by the everted gut sac technique of Martin and DeLuca [Am. J. Physiol. 216, 1351 (1969)] and bone calcium mobilization can be determined by the rise of serum calcium as described for example by Blunt et al. Proc. Nat. Acad. Sci. USA 61, 1503 (1968); degree of endochondral calcification can be assayed by the "line-test" method described in the U.S. Pharmacopeia [15th revision, p. 889, Mack Publ. Easton, Pa. (1955)] using animals maintained on the low phosphorus diet.

Using such methods the biological efficacy of the novel fluorovitamin D compounds of this invention is readily demonstrated. Thus, a 5 μg dose of 25-fluorovitamin $D_2$ administered to vitamin D-deficient, calcium-depleted animals will produce a significant stimulation of intestinal calcium transport and elevation of serum calcium levels within 24 hrs after administration.

Similarly a 1 μg dose of 1α-hydroxy-25-fluorovitamin $D_2$ will be highly effective is stimulating intestinal calcium transport and bone calcium mobilization (as measured by the rise of serum calcium levels), and the compound also promotes the calcification of rachitic bone as measured by the "line test" score.

Fluoro-5,6-trans-vitamin D compounds also exhibit pronounced vitamin D-like activity. For example 25-fluoro-5,6-trans-vitamin $D_3$ is effective in stimulating intestinal calcium transport, bone calcium mobilization and the healing of rickets in these test animals.

It has further been found that the novel 1-fluorovitamin D compounds are biologically potent vitamin D analogs. Thus 1-fluorovitamin $D_3$ administered intraperitoneally to rats maintained on a vitamin D-deficient low-phosphorus diet, causes significant calcification of bone as illustrated in Table 1.

TABLE 1

| Antirachitic Properties of 1-Fluorovitamin $D_3$[a] | | |
|---|---|---|
| Daily dose (ng)[b] | Serum phosphorus (mg/100 ml) | Line-test score |
| 1,2-Propanediol | 3.1 ± 0.3 | 0 |
| Vitamin $D_3$ (20) | 4.5 ± 0.3 | 3.6 ± 0.7 |

TABLE 1-continued

Antirachitic Properties of 1-Fluorovitamin $D_3{}^a$

| Daily dose (ng)[b] | Serum phosphorus (mg/100 ml) | Line-test score |
|---|---|---|
| 1-Fluorovitamin $D_3$ (270) | 4.0 ± 0.2 | 3.2 ± 0.4 |

[a] Data are expressed at mean ± SEM from 3-5 rats.
[b] Test compounds given intraperitoneally in 1,2-propanediol solvent for 7 days.

Similarly, administration of 1-fluorovitamin $D_3$ to vitamin D-deficient animals maintained on a low calcium diet, produces significant elevations of serum calcium levels and will effectivey stimulate intestinal calcium transport, as demonstrated by the typical dose response data given in Table 2.

TABLE 2

Dose Response Data for 1-Fluorovitamin $D_3{}^a$

| Dose (ng)[b] | Bone Calcium Mobilization Serum calcium (mg/100 ml) | Intestinal Calcium transport |
|---|---|---|
| Ethanol (control) | 4.6 ± 0.1 | 1.7 ± 0.2 |
| Vitamin $D_3$ (24) | 5.2 ± 0.2 | 3.1 ± 0.3 |
| 1-Fluorovitamin $D_3$ (280) | 5.1 ± 0.02 | 2.0 ± 0.2 |
| 1-Fluorovitamin $D_3$ (700) | 5.5 ± 0.2 | 2.7 ± 0.2 |
| 1-Fluorovitamin $D_3$ (1260) | 5.8 ± 0.1 | 3.8 ± 0.4 |
| 1-Fluorovitamin $D_3$ (2450) | 6.2 ± 0.3 | 2.8 ± 0.2 |

[a] Data given as mean ± SEM for 5-6 rats.
[b] Compounds administered by intrajugular injections in 50 μl of ethanol solvent.

Having thus described the invention, what is claimed is:

1. Compounds having the formula

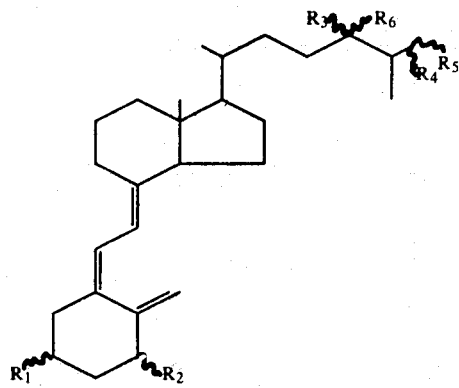

where $R_1$ is selected from the group consisting of hydrogen, hydroxy, O-acyl and O-lower-alkyl, and where $R_2$ is fluoro and where each of $R_3$, $R_4$, and $R_5$ is selected from the group consisting of hydrogen, hydroxy, O-lower-alkyl, O-acyl, lower-alkyl and fluoro, and $R_6$ is hydrogen or lower alkyl.

2. The compounds of claim 1 wherein $R_4$ is hydrogen, hydroxy or fluoro.

3. The compounds of claim 2 wherein $R_3$ is hydrogen, hydroxy or fluoro.

4. 1-fluoro-vitamin $D_3$.

* * * * *